United States Patent
Stiller (10) Patent No.: US 6,803,018 B1
(45) Date of Patent: Oct. 12, 2004

(54) TRANSPORT DEVICE FOR SAMPLE HOLDERS WITH MEDICAL SPECIMENS

(75) Inventor: Bernd Stiller, Hannover (DE)

(73) Assignee: Helmut Goldbecker, Isernhagen (DE)

( * ) Notice: Subject to any disclaimer, the term of this patent is extended or adjusted under 35 U.S.C. 154(b) by 348 days.

(21) Appl. No.: 09/101,663

(22) PCT Filed: Feb. 6, 1997

(86) PCT No.: PCT/DE97/00270
§ 371 (c)(1),
(2), (4) Date: Jul. 14, 1998

(87) PCT Pub. No.: WO97/30355
PCT Pub. Date: Aug. 21, 1997

(30) Foreign Application Priority Data

Feb. 17, 1996 (DE) ......................................... 196 05 977

(51) Int. Cl.⁷ ............................................. G01N 35/00
(52) U.S. Cl. ........................... 422/65; 422/63; 422/104; 436/43; 436/46
(58) Field of Search ........................... 422/63, 65, 104; 436/46, 43; 118/423, 425; 427/2.1, 2.11, 4

(56) References Cited

U.S. PATENT DOCUMENTS

| | | | | |
|---|---|---|---|---|
| 3,976,028 A | * | 8/1976 | Howells et al. ................. | 118/6 |
| 4,738,824 A | * | 4/1988 | Takeuchi ...................... | 422/63 |
| 5,439,649 A | * | 8/1995 | Tseung et al. ................. | 422/99 |
| 5,573,727 A | * | 11/1996 | Keefe ........................... | 422/63 |
| 5,895,628 A | * | 4/1999 | Heid et al. .................... | 422/65 |

FOREIGN PATENT DOCUMENTS

| | | |
|---|---|---|
| DE | 1923810 | 2/1970 |
| DE | 4117833 C2 | 10/1993 |

* cited by examiner

Primary Examiner—Jill Warden
(74) Attorney, Agent, or Firm—Collard & Roe, P.C.

(57) ABSTRACT

A transport device conveys sample holders with medical specimens to and from treatment stations as well as sampling and dispensing stations within an autosampler. The transport device consists of a carriage which is conveyable horizontally along at least one axis with a vertically conveyable hoisting device and, arranged on the hoisting device, a coupling element for the sample holder. A collecting device to catch any liquid dripping from the sample holder can be placed underneath the sample holder during transport.

8 Claims, 13 Drawing Sheets

TRANSPORT DEVICE FOR SAMPLE HOLDERS WITH MEDICAL SPECIMENS

The invention relates to a transport device for sample holders with medical specimens according to the preamble of claim 1.

German Patent No. 4,117,833 C2 discloses a device for staining histological preparations arranged on microscope slides. With this device, a matrix arrangement of treatment stations is provided and can be approached by a triaxial control. Multiple treatment operations can also be performed simultaneously with different staining programs in parallel.

To prevent contamination of the treatment stations with treatment reagents from other treatment stations, the microscope slide holders, after leaving one treatment station with liquid reagents, are conveyed to the next treatment station over a separate drip zone. The drip zone is arranged as a water carrying chamber between two parallel rows of treatment stations. Therefore, the time needed for dripping can also be utilized for conveyance.

However, the space required by the drip zone limits the possibility of accommodating additional treatment stations in the same base area.

The object of the invention is to improve on a transport device for sample holders with medical preparations such that contamination of the treatment stations with treatment reagents from other treatment stations is prevented without separate drip zones.

This object is achieved with a transport device according to the preamble of claim 1 by the features given in the characterizing part.

Refinements and advantageous embodiments are derived from the subclaims.

In the design according to the present invention, the collecting device is always entrained together with the carriage holding the hoisting device, so that the collecting device requires very little space. The space required previously by the separate drip zone is eliminated, and it is either possible to have additional treatment stations occupy the area taken up previously by the drip zone or, if the number of different treatment stations is kept the same, they may be accommodated more compactly. Furthermore, the sample holder may be conveyed in the direction of all axes at the same time. This permits a great reduction in transport times, which has an especially favorable effect when there are staining programs running in parallel, sometimes with very short dwell times of the preparations in the treatment stations.

A more compact accommodation of the treatment stations also has the advantage that the autosampler can be reduced in size and thus the transport paths can be shortened. This leads to a further reduction in transport times.

The collecting device may be designed as a collecting pan which can be swivelled vertically or horizontally relative to the hoisting device. In addition or as an alternative, the hoisting device may also be swivelled vertically or horizontally relative to the collecting pan. This design is characterized by an especially simple bearing arrangement.

Furthermore, the collecting device may also be designed as a collecting pan which can be moved horizontally relative to the hoisting device. In addition or as an alternative, the hoisting device may also be movable horizontally relative to the collecting pan. This permits a reduction in vertical space required for the collecting device.

The collecting device can be designed to be especially space saving if the collecting pan is made of a flexible material. Then, when it is moved, the collecting pan can be simply deflected from the vertical starting position to the horizontal collecting position.

The collecting pan may also include a liquid reservoir. This may be designed as a trough or a sponge. When designed as a trough, the liquid reservoir can be emptied automatically from time to time. The sponge design, however, is more suitable for manual emptying. However, it has the advantage that no collected fluid can splash out during rapid movements.

The hoisting device preferably includes a vibrating device which may be implemented, for example, by rapidly changing the direction of movement of the hoisting device. Thus, the dripping process can be accelerated and intensified so that, even with short transport paths, there need be no waiting time until the sample holder can be turned over to the next treatment station.

The coupling element can also be swivelled into a coupled position and a release position by means of a separate coupling drive. The coupling and uncoupling operations can be accelerated in this way.

The invention is explained below with reference to the figures, which show.

transport devices for sample holders in different embodiments.

The diagram of the transport devices is limited here to a carriage 12, which can be moved horizontally in one axis, with a vertically movable hoisting device 14 and a coupling element 16 for a sample container 10 arranged on hoisting device 14. If the possibility of biaxial conveyance in the horizontal direction is required, the carriage 12 shown here may be arranged on a second carriage which can be conveyed at a right angle to the first carriage 12.

The hoisting device 14 comprises a vertical rail 24 with a toothed profile 26 and a sample carriage 28. Sample carriage 28 is either mounted so it can slide on rail 24, and then it has a drive with a pinion that engages in tooth profile 26 of rail 24, or the sample carriage 28 is fixedly connected to rail 24 and is conveyed together with the rail by means of a drive arranged on the horizontally movable carriage 12. A coupling element 16 for a sample holder 10 is attached to sample carriage 28. Coupling element 16 is designed here as a hook in which rests the shackle of a sample holder 10.

Furthermore, a collecting device 18 for fluid dripping off the sample holder 10 is also provided. Collecting device 18 comprises a suspension 30 which is next to the vertical rail 24 and holds a collecting pan 20; 22 on its lower end. The collecting pan may be designed in one or more parts.

Figure 1A:
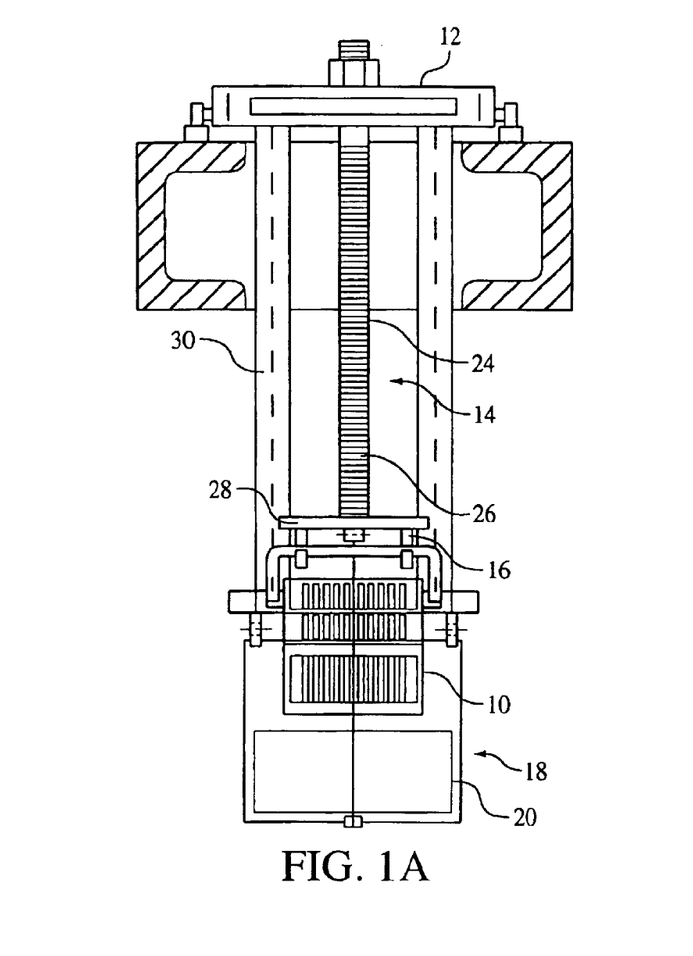
FIGS. 1A and 1B show two views of a first embodiment.
Figure 1B:
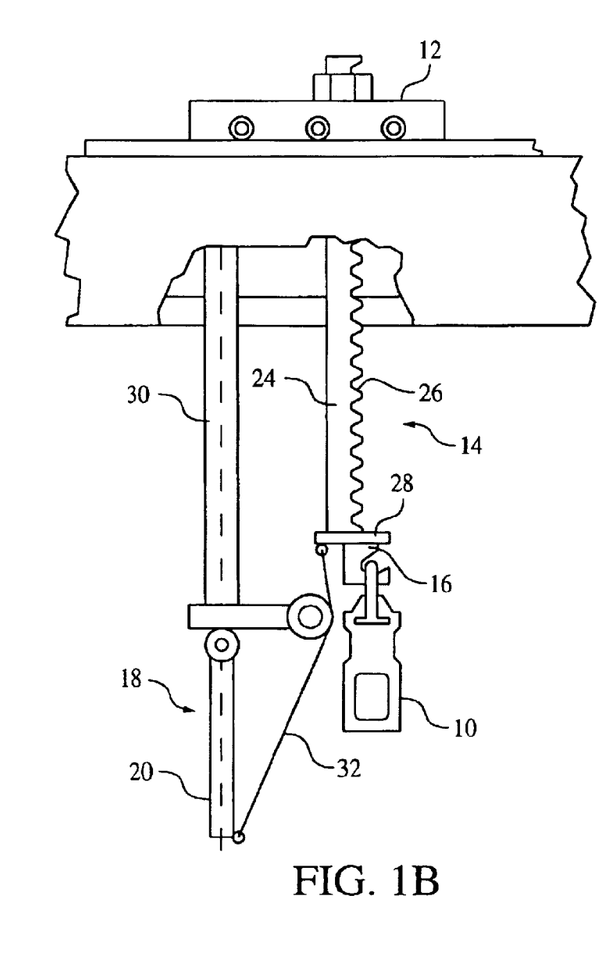

FIGS. 1A and 1B shows two views of an embodiment where a collecting pan 20 can be swivelled up from below about a horizontal axis, from a vertical starting position into a horizontal collecting position. Collecting pan 20 is coupled to sample carriage 28 by a cable 32 and is thus automatically swivelled in the hoisting operation.

Figure 2A:
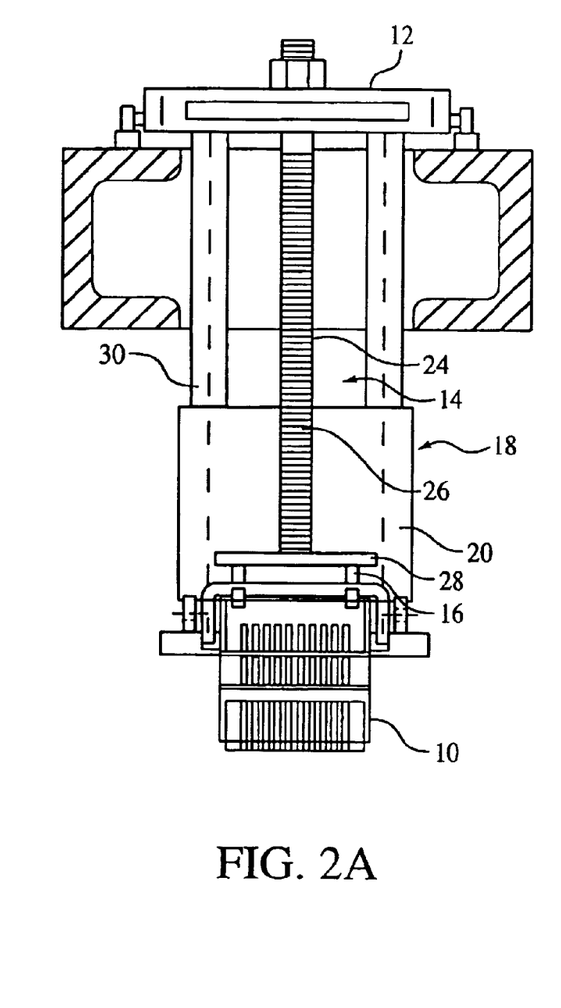
FIGS. 2A and 2B show two views of a embodiment similar to that in FIGS. 1A and 1B.
Figure 2B:
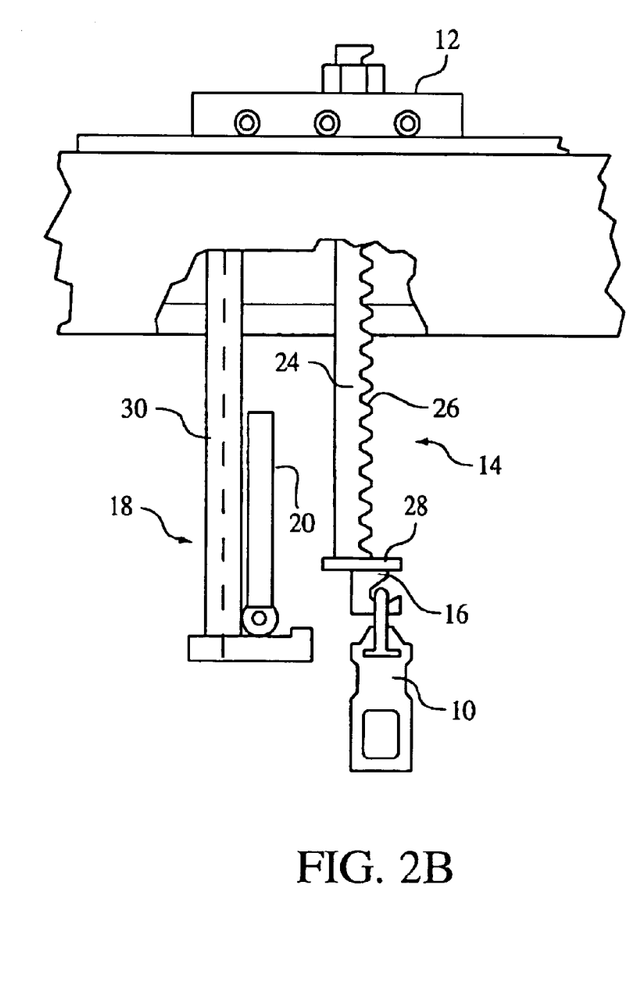

FIGS. 2A and 2B show two views of an embodiment similar to that in FIGS. 1A and 1B but here the collecting pan 20 is swivelled down from above out of a vertical starting position.

Figure 3A:
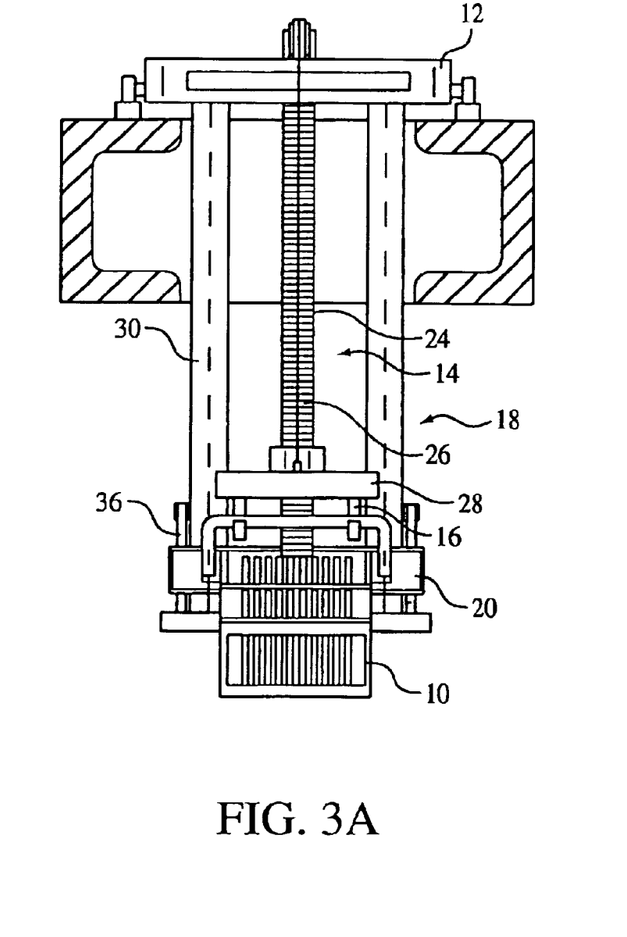
FIGS. 3A and 3B show two views of a third embodiment.
Figure 3B:
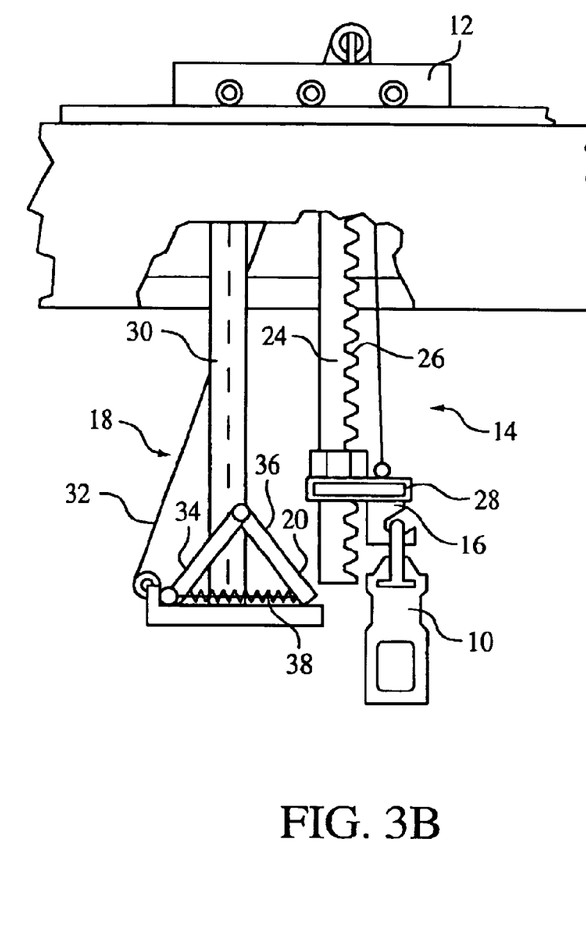

FIGS. 3A and 3B shows two views of one embodiment, where a collecting pan 20 is hinge-connected to suspension 30 by hinged legs 34, 36. Legs 34, 36 are under the initial tension of a spring 38. A cable 32 attached to collecting pan 20 runs over two pulleys to sample carriage 28. When sample carriage 28 is raised, spring 38 is extended, and the legs 34, 36 are spread apart, so that the collecting pan 20 goes beneath the sample holder 10. When the sample carriage 28 is lowered, the legs 34, 36 are folded together again, thereby compressing the spring 38.

Figure 4A:
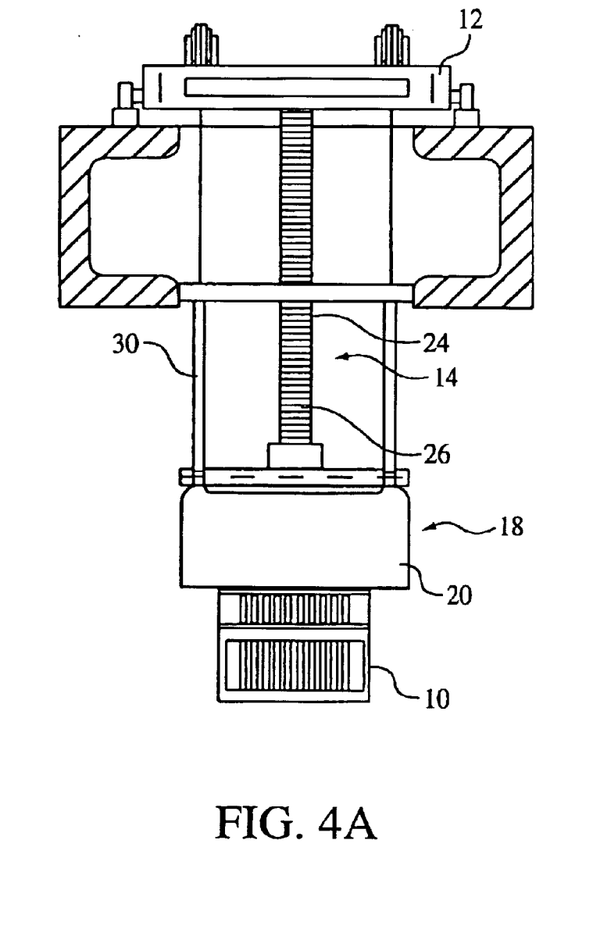
FIGS. 4A and 4B show two views of a fourth embodiment.
Figure 4B:
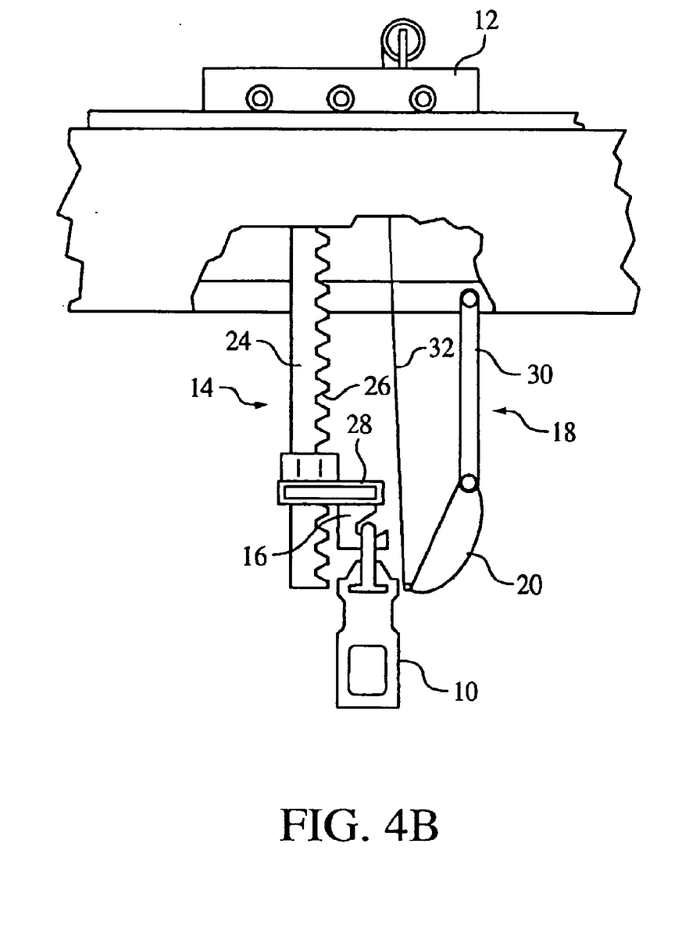

FIGS. 4A and 4B show two views of one embodiment, where a collecting pan 20 is hinge-connected to the suspension 30, and suspension 30 is in turn hinge-connected to the carriage 12, which can move horizontally. The collecting pan 20 is operated by a cable 32.

Figure 5A:
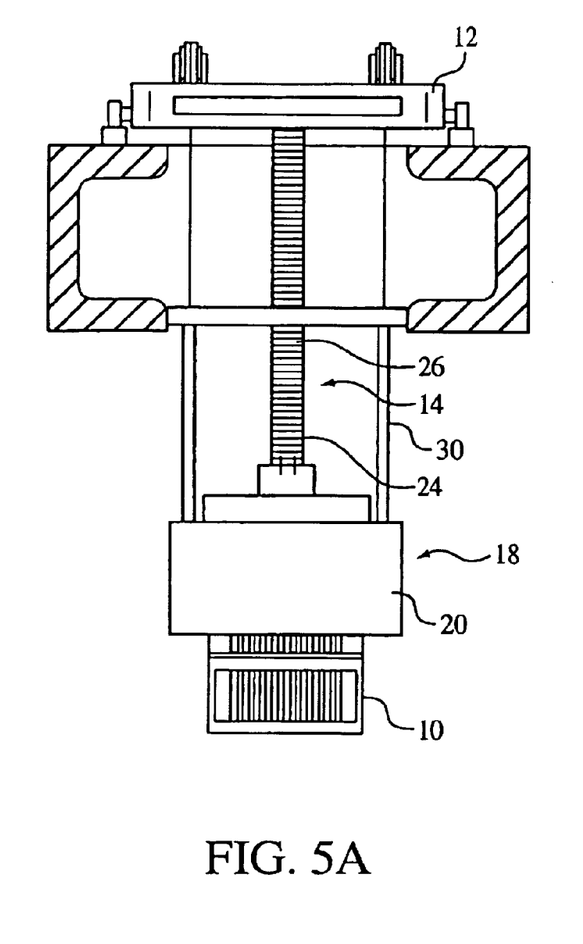
FIGS. 5A and 5B show two views of a fifth embodiment.
Figure 5B:
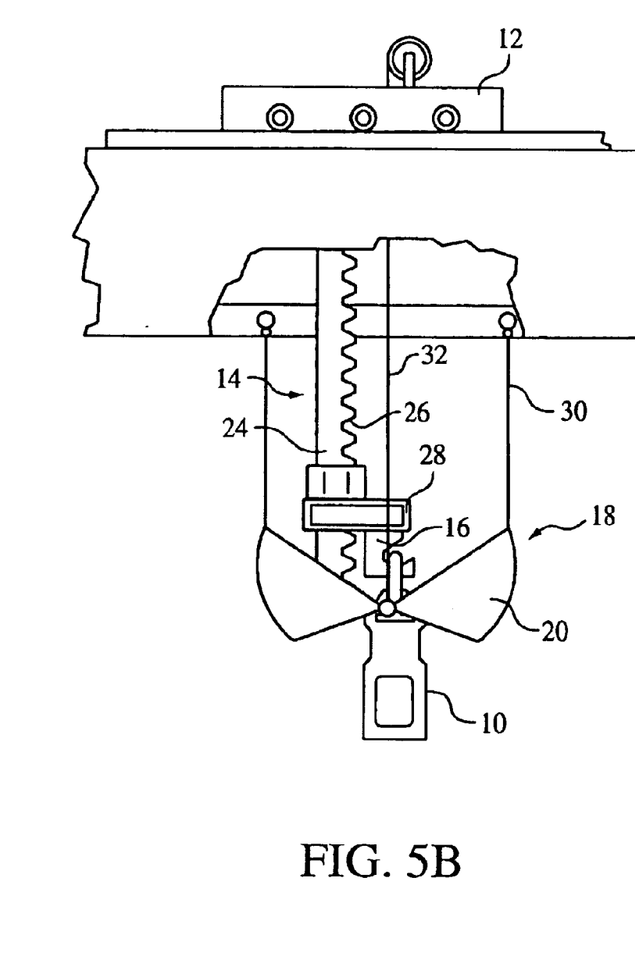

The embodiment according to FIGS. 5A and 5B differs from that according to FIG. 4 in that the collecting pan 20 is in two parts and is operated by a common cable 32 so that it closes beneath the sample carriage 28.

Figure 6A:
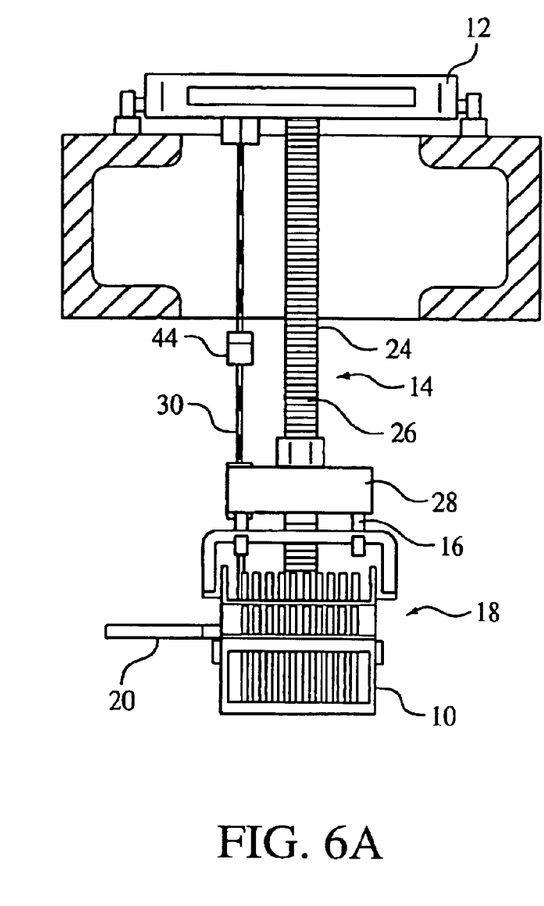
FIGS. 6A and 6B show two views of a sixth embodiment.
Figure 6B:
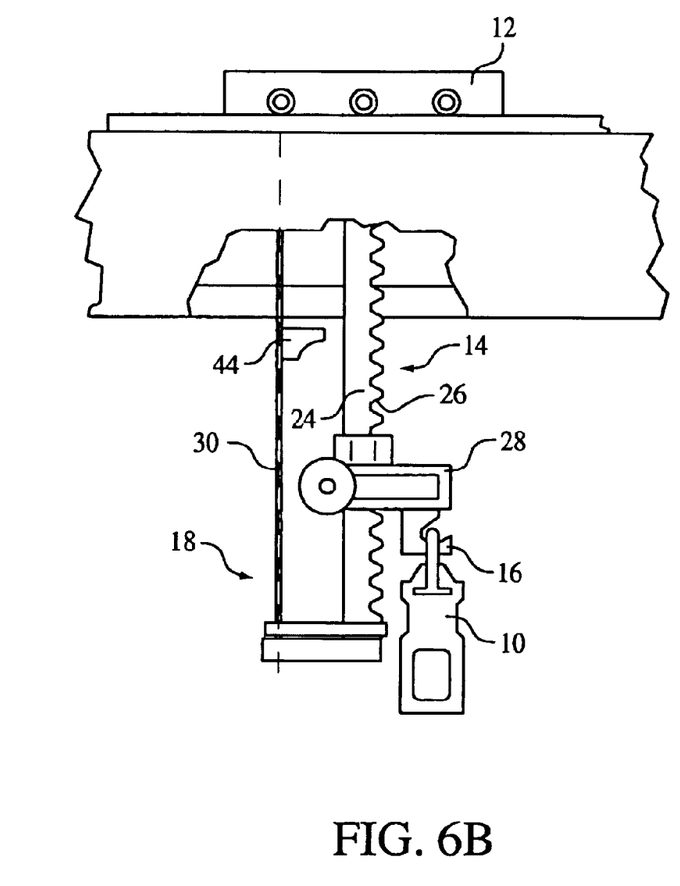

FIGS. 6A and 6B show two views of an embodiment where a collecting pan 20 can be swivelled beneath the sample carriage 28 about a vertical axis. The suspension 30 here is designed as a shaft with a cam 44 which is deflected by the sample carriage 28.

Figure 7A:
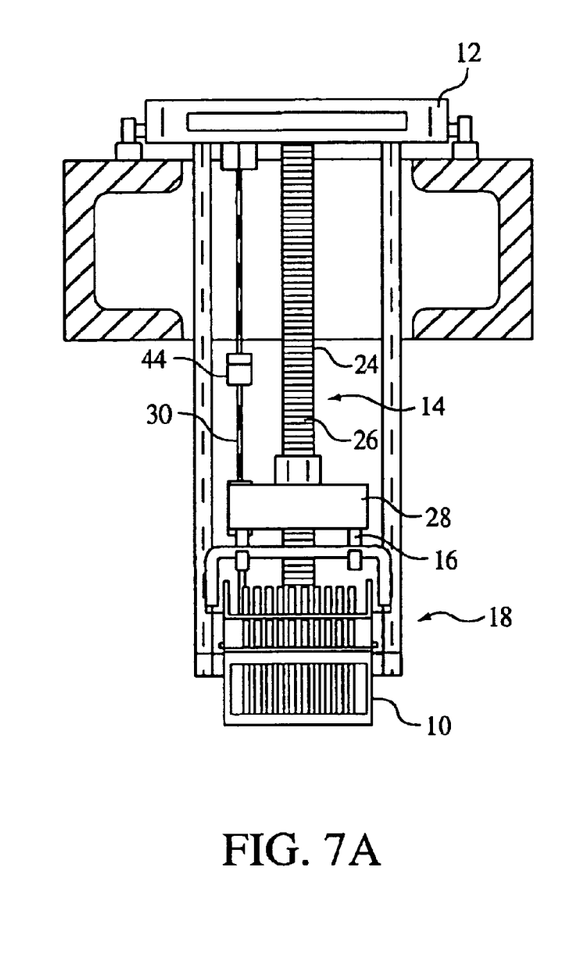
FIGS. 7A and 7B show two views of a seventh embodiment.
Figure 7B:
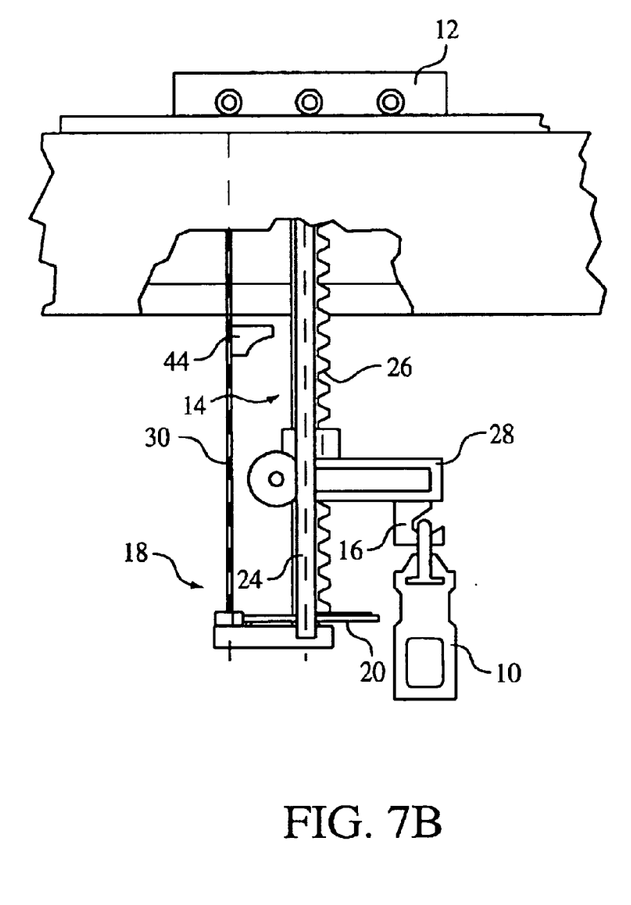

The embodiment shown in, FIGS. 7A and 7B resembles that in FIGS. 6A and 6B but here the collecting pan 20 can be moved horizontally beneath the sample carriage 28 by converting the swiveling movement of the shaft into a linear movement of the collecting pan 20 by means of a toggle lever or a crank gear.

Figure 8A:
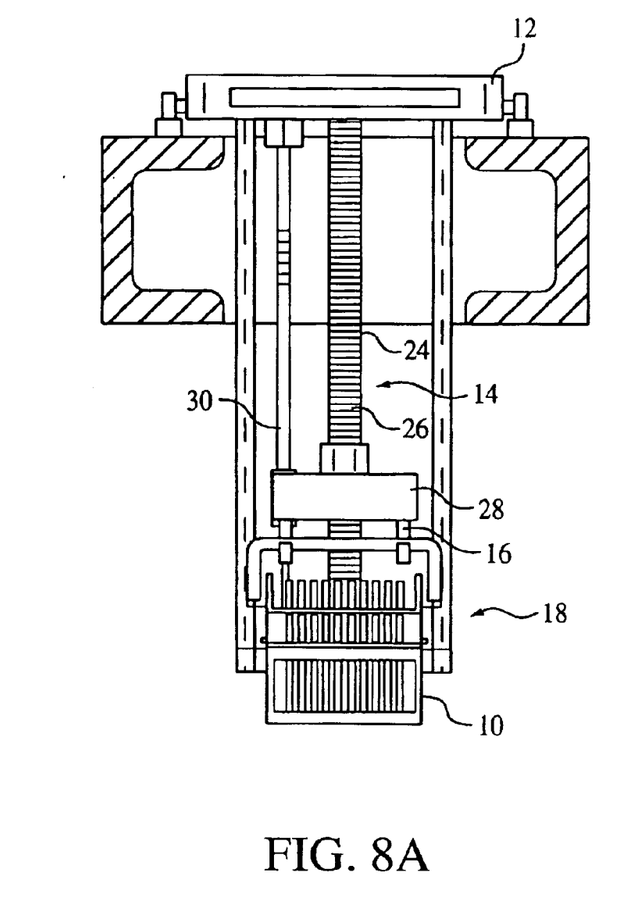
FIGS. 8A and 8B show two views of a eighth embodiment.
Figure 8B:
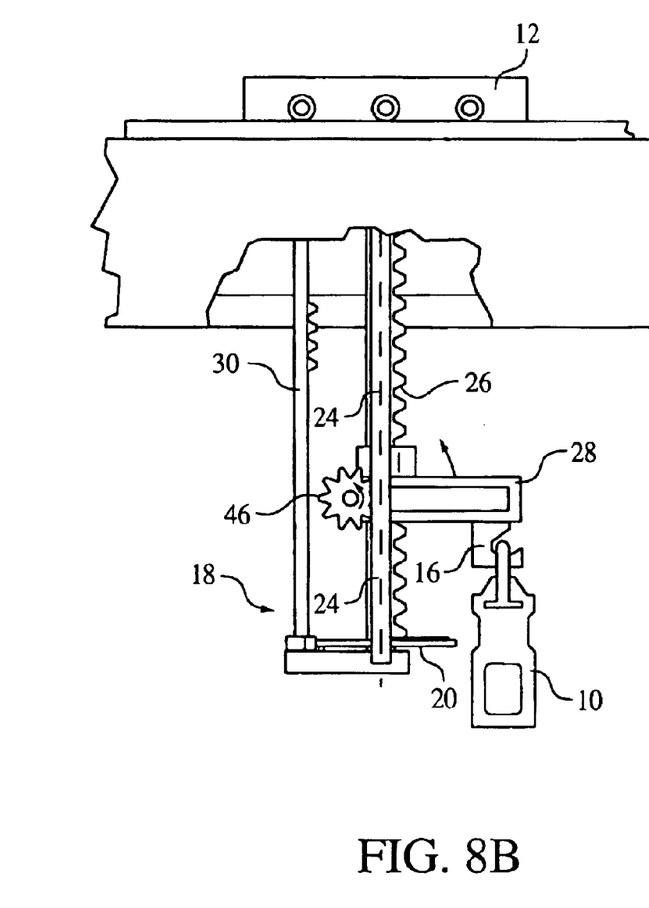

FIGS. 8A and 8B show a embodiment where the sample carriage 28 is swivelled about a horizontal axis as soon as a cam 46 strikes a stop when lifted by the hoisting device 14.

Figure 9:
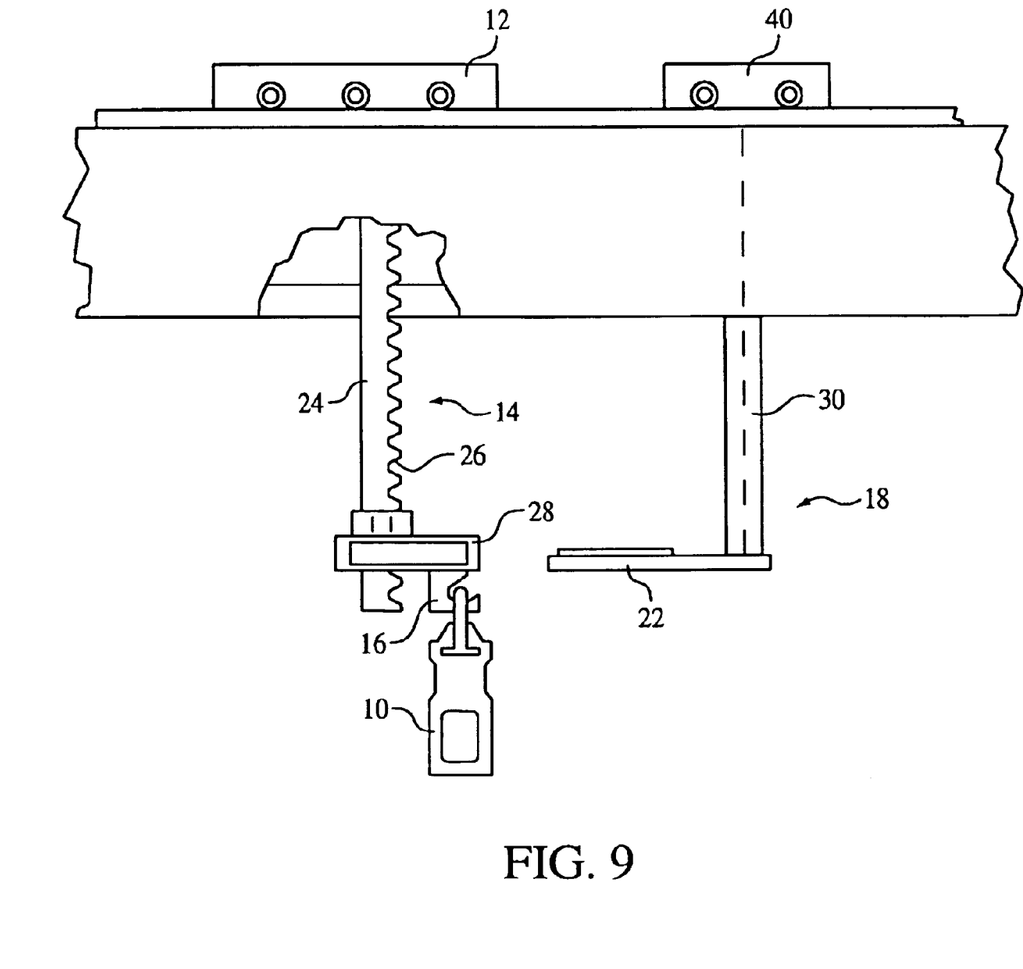
FIG. 9 shows a ninth embodiment.

In an embodiment illustrated in FIG. 9, the suspension 30 is arranged with a collecting pan 22 on a separate carriage 40 and can be moved horizontally relative to the carriage 12 for the hoisting device 14.

Figure 10A:
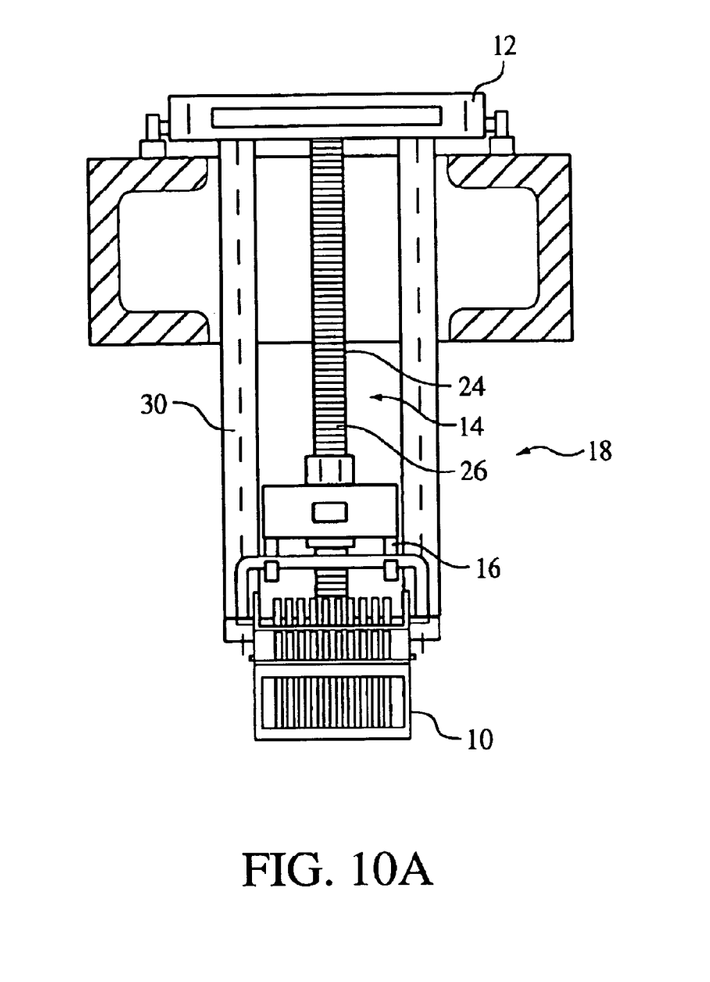
FIGS. 10A and 10B show two views of a tenth embodiment.
Figure 10B:
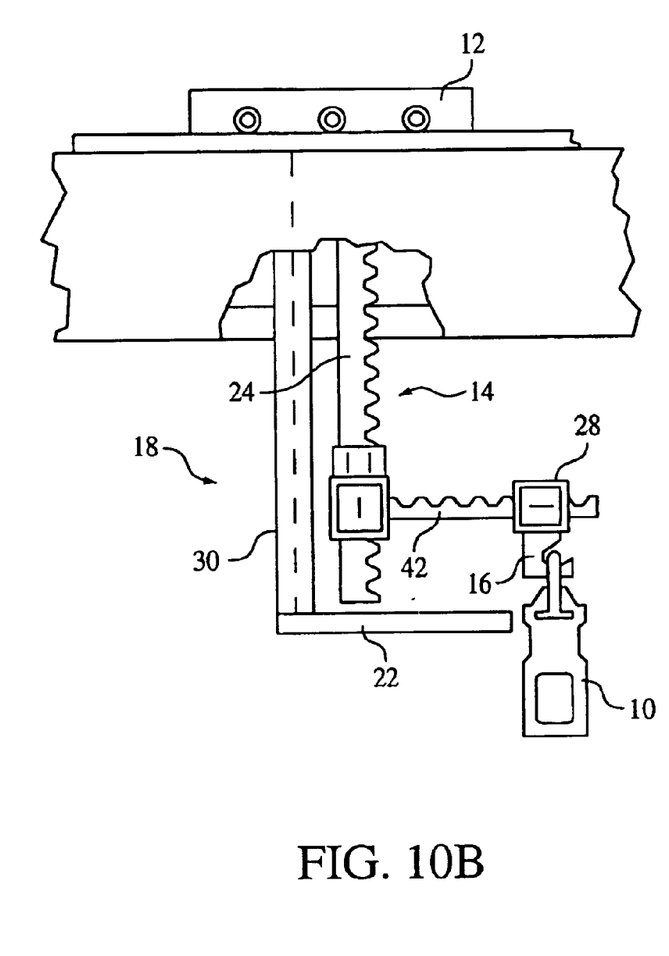

FIGS. 10A and 10B show two views of one embodiment, where a collecting pan 22 is fixedly attached to a suspension 301 and the sample carriage 28 can also be moved horizontally on another rail 42 by means of a separate drive.

Figure 11A:
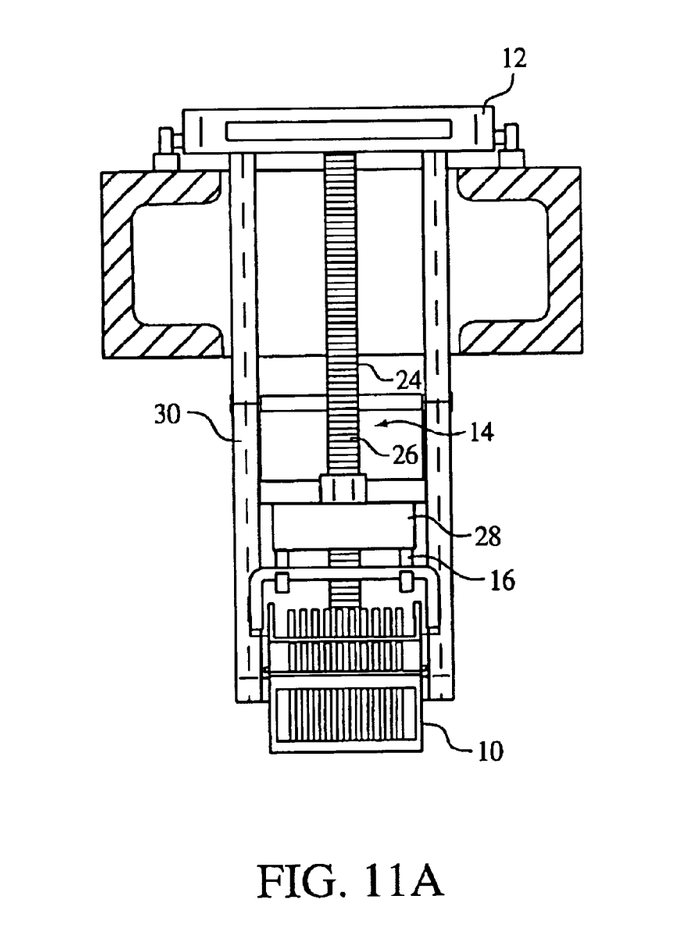
FIGS. 11A and 11B show two views of a eleventh embodiment.
Figure 11B:
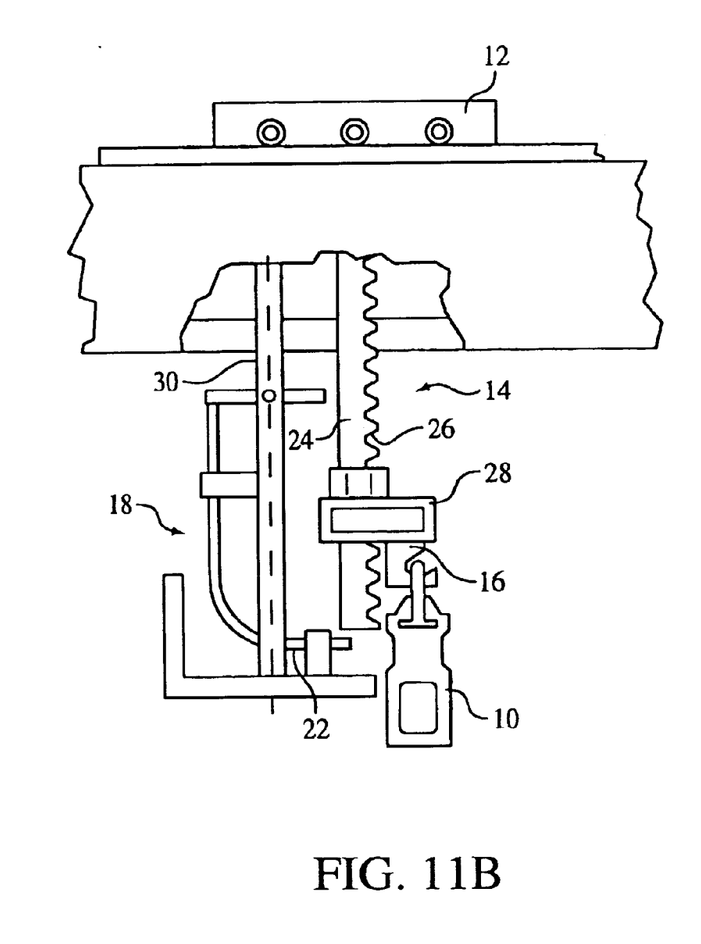
Figure 12A:
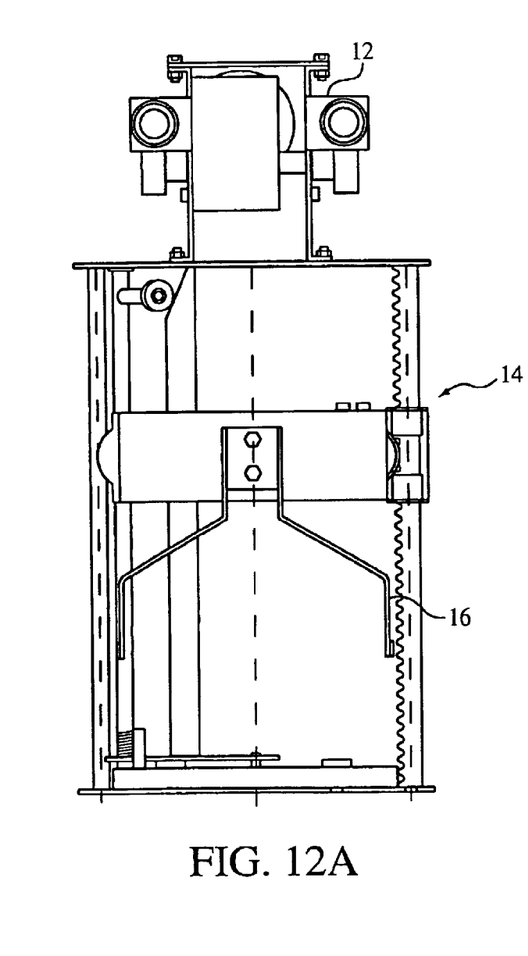
FIGS. 12A, 12B and 13A, 13B each show two views of a twelfth and thirteenth embodiment respectively.
Figure 12B:
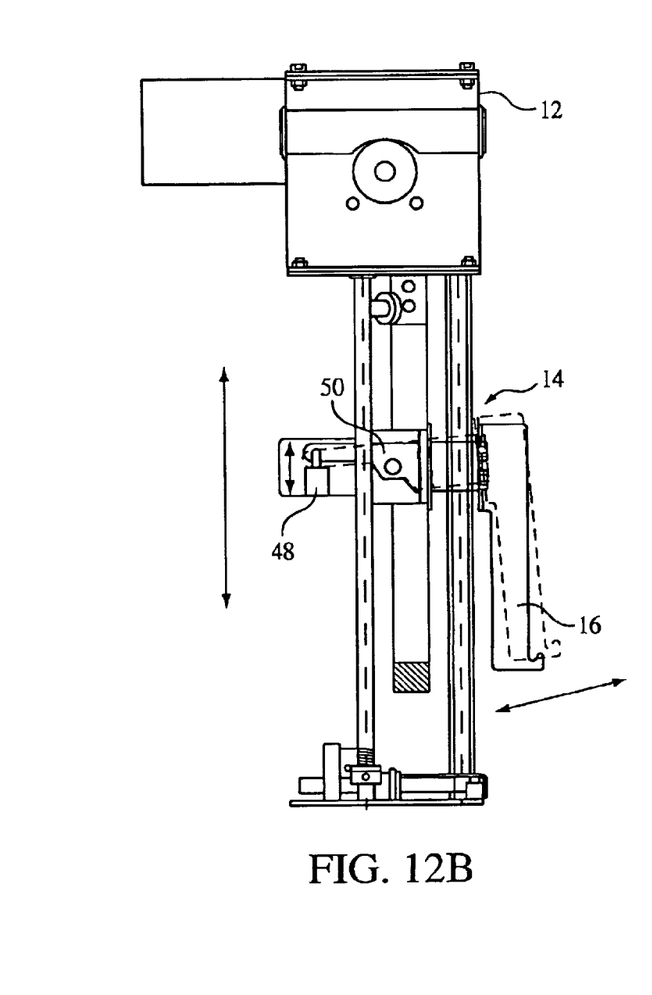
Figure 13A:
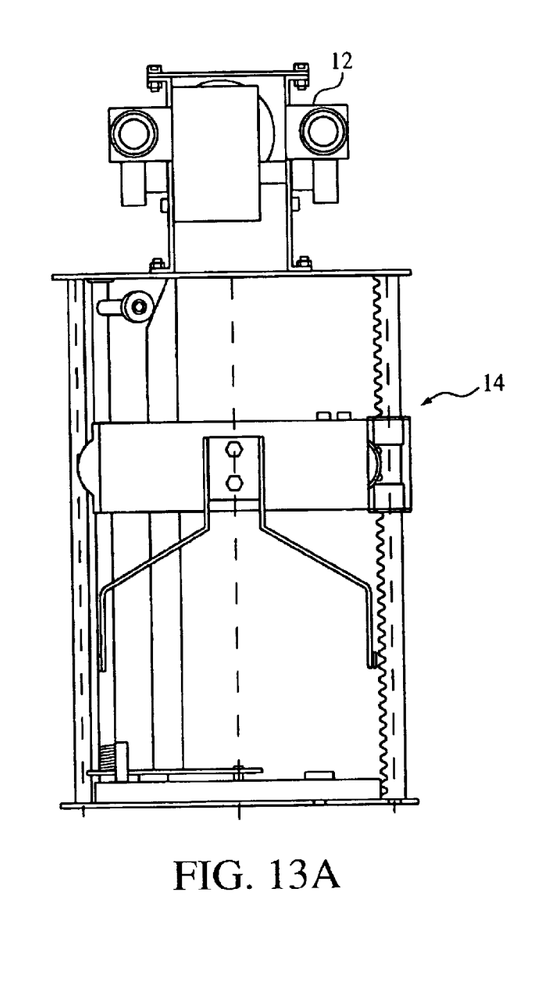
Figure 13B:
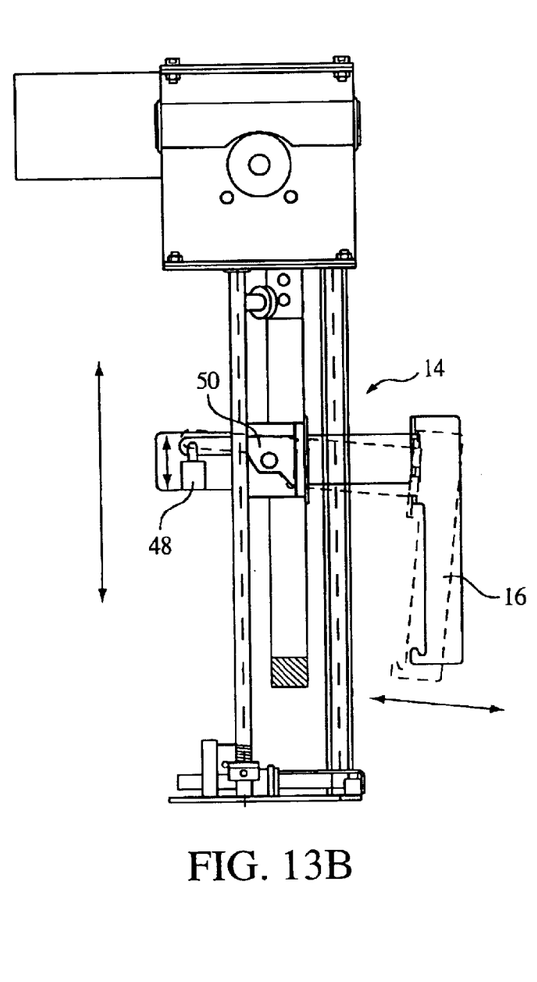

FIGS. 11A and 11B show two views of one embodiment where a collecting pan 22 is made of a flexible material, preferably spring steel, and is deflected into the horizontal direction when displaced, so that it comes under the sample carriage 28.

The collecting pans 20, 22 include the liquid reservoir. In the embodiments where the collecting pan 20, 22 is oriented only horizontally, a trough is sufficient for this purpose. A sponge is preferably provided with the collecting pans that can be pivoted about a horizontal axis, so that all the liquid is stored even in the vertical starting position.

An additional vibrating device of the hoisting device 14 accelerates and intensifies the dripping process.

FIGS. 12A, 12B, and 13A, 13B each show two views of two embodiments where the coupling element 16 can be swivelled into a coupled position and into a release position by means of a separate coupling drive 48. In the coupled position, the recess and the tip of each hook are higher than in the release position, and furthermore, the difference in height between the tip and the recess of each hook is greater in the coupled position than in the release position. The coupling element 16 is attached to an arm of a rocker 50 which can be pivoted about a horizontal axis. The coupling drive 48 acts on the opposite arm of the rocker. Since the coupling drive 48 must perform only small hoisting movements, it may be designed as an electromagnet, and it can therefore switch very rapidly.

The transport device described here is used preferably in automatic staining systems for histological and cytological staining and in staining for gel electrophoresis and in automatic tissue embedding systems and automatic tissue dehydrating systems. As soon as a sample holder 10 with specimens is lifted out of a treatment station with liquid reagents, a collecting pan 20, 22 is placed under the sample holder 10. Reagents dripping off thus enter the collecting pan 20, 22. Due to a vibrating movement of the sample holder 10, excess reagents are additionally shaken off while the sample holder 10 is being conveyed to the next treatment station. When it arrives there, the collecting pan 20, 22 is removed again, and the sample holder 10 is lowered into the next treatment station.

What is claimed is:

1. A transport device for conveying at least one sample holder containing a medical specimen comprising:
   (a) a carriage conveyed horizontally in at least one axis;
   (b) a vertically movable hoisting device;
   (c) a coupling element for the sample holder arranged on the hoisting device;
   (d) a collecting device for liquid dripping off the sample holder positioned beneath the sample holder while the sample holder is being conveyed.

2. A transport device according to claim 1 wherein the collecting device comprises a collecting pan pivotably mounted relative to the hoisting device in a horizontal or vertical direction.

3. A transport device according to claim 1 wherein the collecting device comprises a movable collecting pan conveyed horizontally relative to the hoisting device.

4. A device according to claim 3 wherein the collecting pan is made of a flexible material.

5. A device according to claim 1 wherein the collecting pan includes a liquid reservoir.

6. A device according to claim 5 wherein the liquid reservoir is selected from the group consisting of a trough and a sponge.

7. A device according to claim 1 wherein the hoisting device includes a vibrating device.

8. A device according to claim 1 further comprising a coupling drive pivoting the coupling element into a coupled position and a release position.

* * * * *